United States Patent
Shirasuka

[19]
[11] Patent Number: 6,033,217
[45] Date of Patent: Mar. 7, 2000

[54] ORTHODONTIC DEVICE

[75] Inventor: Masako Shirasuka, Tokyo, Japan

[73] Assignee: Shofu Inc., Kyoto, Japan

[21] Appl. No.: 09/214,842

[22] PCT Filed: May 16, 1997

[86] PCT No.: PCT/JP97/01657

§ 371 Date: Jan. 14, 1999

§ 102(e) Date: Jan. 14, 1999

[87] PCT Pub. No.: WO98/51230

PCT Pub. Date: Nov. 19, 1998

[51] Int. Cl.[7] .................. A61C 7/12; A61C 7/18
[52] U.S. Cl. ............................... 433/18; 433/24
[58] Field of Search ................... 433/7, 18, 19, 433/21, 23, 24

[56] References Cited

U.S. PATENT DOCUMENTS

| | | |
|---|---|---|
| 3,353,271 | 11/1967 | Blechman . |
| 3,936,938 | 2/1976 | Northcutt . |
| 4,202,100 | 5/1980 | Förster ........................ 433/22 |
| 4,592,725 | 6/1986 | Goshgarian ................ 433/24 |
| 5,022,855 | 6/1991 | Jeckel .......................... 433/18 |
| 5,443,384 | 8/1995 | Franseen et al. ........... 433/18 |
| 5,829,970 | 11/1998 | Yousefian .................. 433/21 |
| 5,871,350 | 2/1999 | Clark et al. ................. 433/18 |
| 5,873,716 | 2/1999 | Kesling ....................... 433/22 |

FOREIGN PATENT DOCUMENTS

| | | |
|---|---|---|
| 53-55694 | 5/1978 | Japan . |
| 60-88908 | 6/1985 | Japan . |
| 62-286457 | 12/1987 | Japan . |
| 04092657 | 3/1992 | Japan . |
| 04309346 | 10/1992 | Japan . |
| 09135849 | 5/1997 | Japan . |

*Primary Examiner*—Ralph A. Lewis
*Attorney, Agent, or Firm*—Stevens, Davis, Miller & Mosher, L.L.P.

[57] ABSTRACT

An orthodontic appliance comprises a band to be set around one tooth of lateral teeth, an outer cylinder fixed to the band, an inner cylinder formed longer than the outer cylinder and supported slidably within the outer cylinder, a wire fixed to each tooth of anterior teeth via a bracket and extended toward the lateral teeth, and inserted through the inner cylinder, and biasing means attached between the outer cylinder and the bracket and serving for biasing the anterior teeth toward the lateral teeth, in which arrangement the inner cylinder is fixed at an open end portion to the wire.

7 Claims, 4 Drawing Sheets

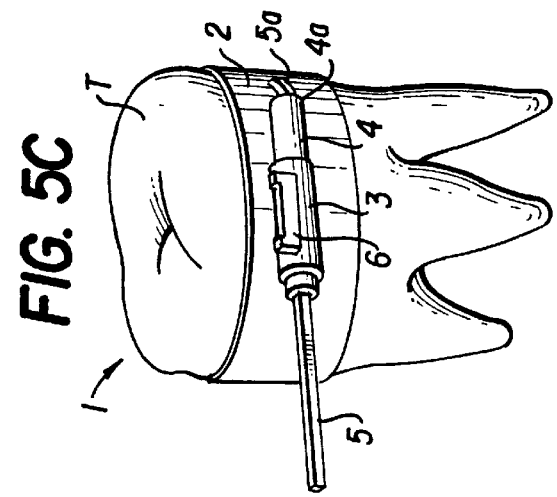
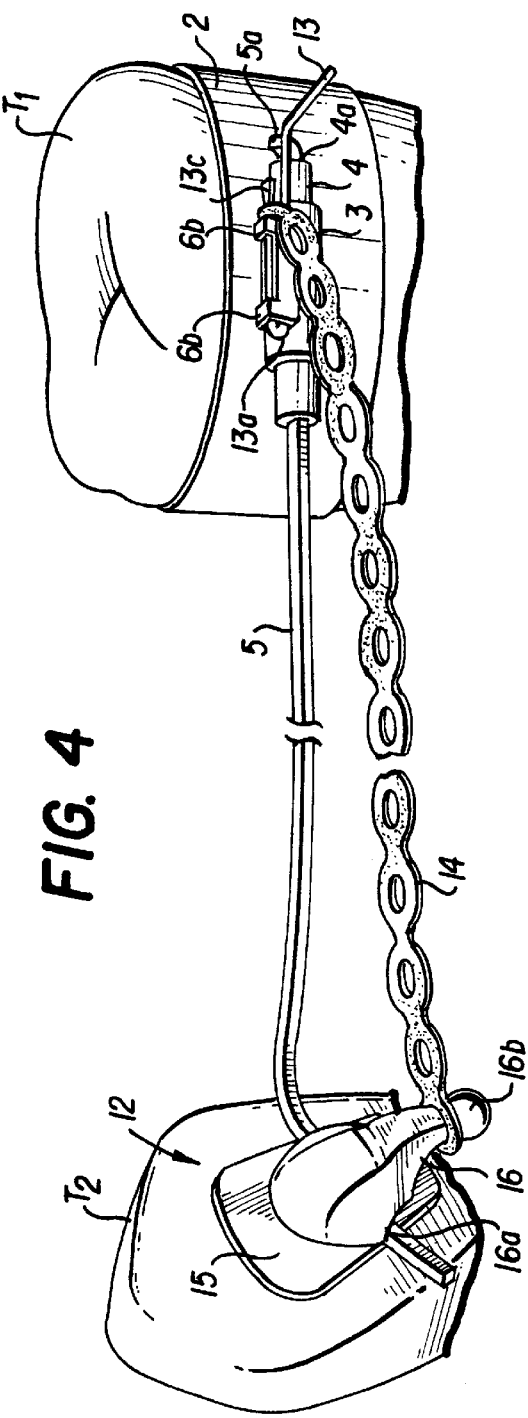
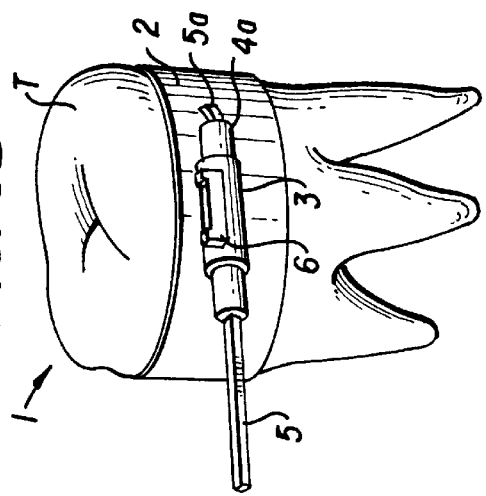
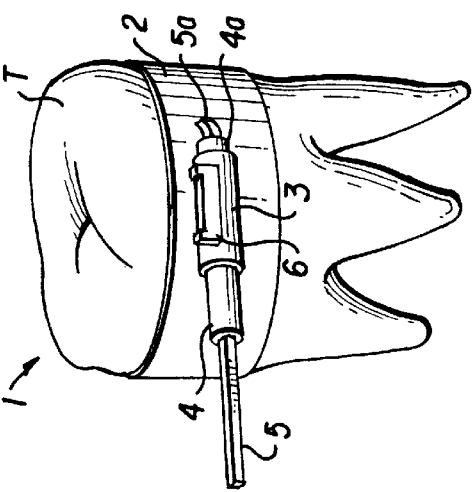

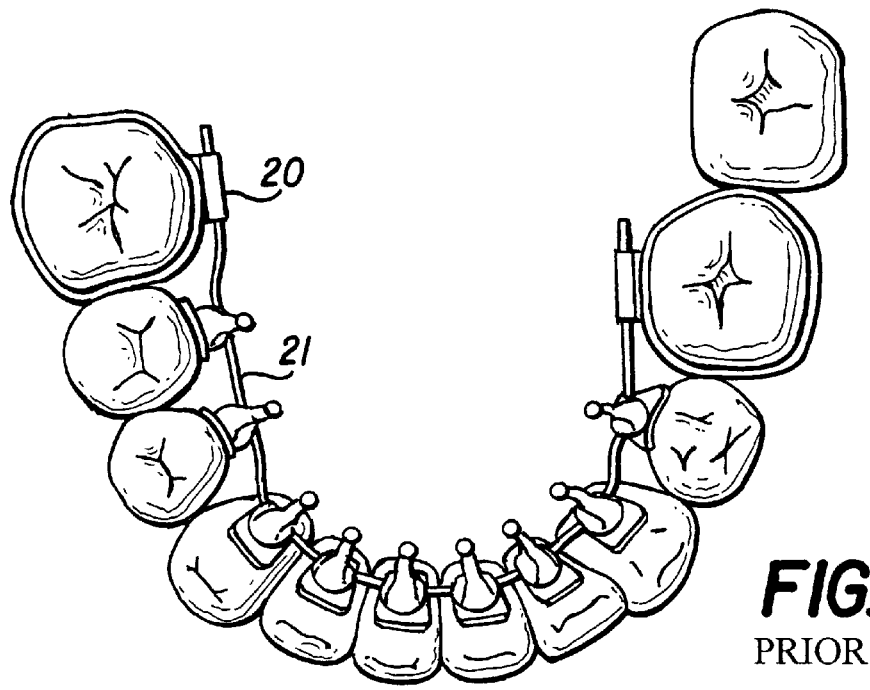
FIG. 7
PRIOR ART
FIG. 8
PRIOR ART
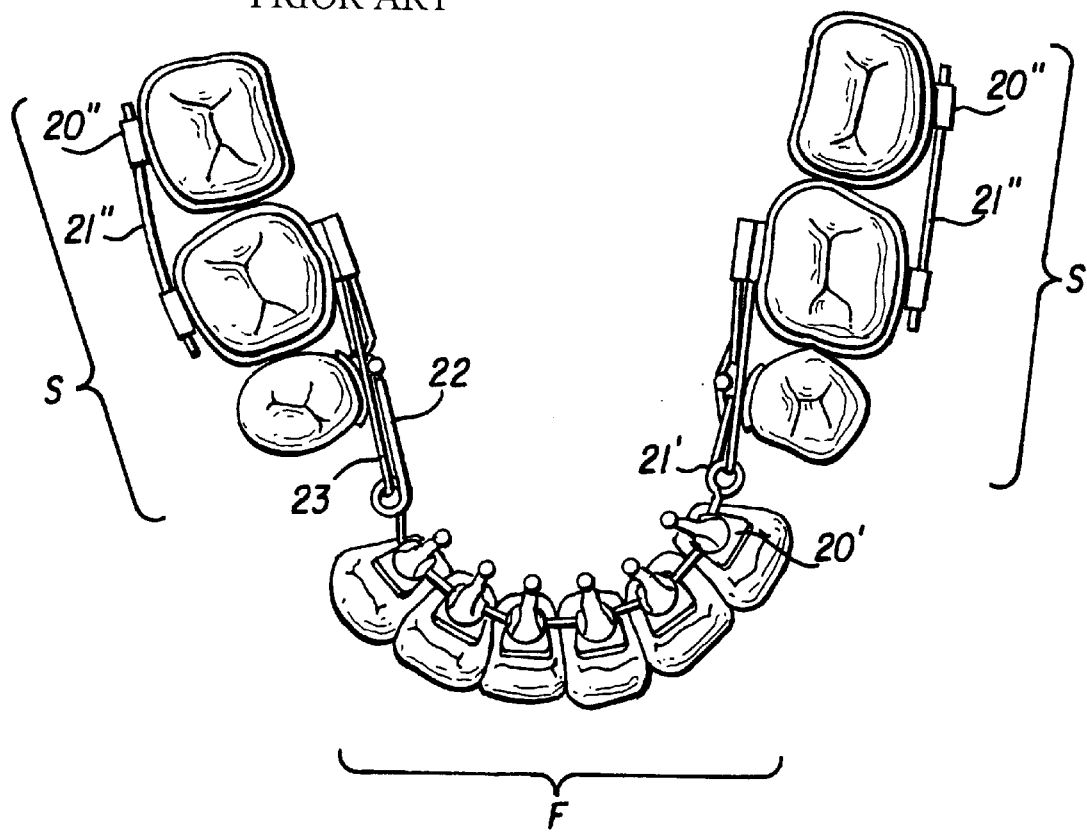

6,033,217

ORTHODONTIC DEVICE

TECHNICAL FIELD

The present invention relates to orthodontic appliances, and more particularly to a slidable orthodontic appliance to be used in coupling anterior teeth and lateral teeth to each other.

BACKGROUND ART

As a method of orthodontic, there has conventionally been employed, for example, a method comprising steps of extracting the first premolar tooth or the like and retracting anterior teeth toward lateral teeth to align the remaining teeth. In such a case, a technique of using an orthodontic metal wire 21 made of stainless steel attached to a large number of brackets 20 fixed to the teeth is available as shown FIG. 6.

The technique shown in FIG. 6, however, has a disadvantage of spoiling the appearance of teeth because the metal wire is placed buccally. For this reason, another technique of placing the brackets 20 and the metal wire 21 lingually is also available, as shown in FIG. 7. In this technique, however, the brackets and metal wire are not easy to set.

Therefore, a technique shown in FIG. 8 is also adopted in some cases, where brackets 20' and a metal wire 21' are set on the lingual side of the anterior teeth F only, while, for lateral teeth S, brackets 20" and a metal wire 21" are provided on the buccal side of the lateral teeth S, the lateral teeth S and the anterior teeth F are coupled to each other with metal wires 22 and further the anterior teeth F is pulled toward the lateral teeth S by biasing means 23 such as elastic modules.

In the technique shown in FIG. 8, however, as the anterior teeth F is supported only by the metal wires 22, the metal wires 22 deflect, causing obstruction to the tooth alignment. While the tooth alignment, since the biasing means 23 keeps biasing the anterior teeth F toward the lateral teeth S, the distance between the anterior teeth F and the lateral teeth S becomes shorter gradually with a lapse of time. Unfortunately, because no means of absorption therefor is provided, the metal wire 22 would need to be readjusted for its shape, length and the like. As a result, this work would cause a complexity.

DISCLOSURE OF THE INVENTION

The present invention has been achieved in view of these and other disadvantages of the conventional orthodontic appliance and method.

It is an object of the invention to provide an orthodontic appliance which is capable of firmly coupling anterior teeth and lateral teeth to each other while preventing any deflection of the wire and which enhances working efficiency when setting the orthodontic appliance.

It is another object of the present invention to provide an orthodontic appliance which is free from any spoilage of the appearance of teeth and which is also capable of simultaneously aligning teeth with an outer cylinder mounted thereto around an axis line vertical to the occlusal surfaces of the teeth.

To achieve the above objects, the present invention provides an orthodontic appliance comprising a band to be set around one tooth of lateral teeth, an outer cylinder fixed to the band, a wire fixed to each tooth of anterior teeth and extended toward the lateral teeth, biasing means for biasing the wire toward the lateral teeth, and an inner cylinder formed longer than the outer cylinder and supported slidably within the outer cylinder, wherein the inner cylinder has such an inside diameter as to allow the wire to be inserted therethrough, and a fixing portion capable of fixing the wire at an open end portion thereof.

In this case, since the inner cylinder is formed longer than the outer cylinder and supported slidably within the outer cylinder, the wire, after being inserted into the inner cylinder, can be set by inserting the inner cylinder into the outer cylinder. Thus, the setting workability of the orthodontic appliance is improved. Also, the anterior teeth and the lateral teeth can be firmly coupled to each other, while the wire is prevented from deflection.

As one embodiment of the present invention, the outer cylinder and the inner cylinder may be preferably located on the lingual side of the lateral teeth. In this case, the orthodontic appliance never spoils the appearance of the teeth.

As another embodiment of the present invention, a lingual sheath may be preferably fixed or fixable to the outer cylinder. In this case, with a simple construction, for the tooth with the outer cylinder mounted thereto, aligning along an axis line vertical to the occlusal surface of the tooth can also be accomplished simultaneously.

As another embodiment of the prevent invention, a transpalatal bar may be preferably attached to the lingual sheath.

Further, as another embodiment of the prevent invention, the inner cylinder may be preferably fixed to the wire by bending the wire protruding from the open end portion of the inner cylinder. In this case, the wire can be prevented from falling off from the inner cylinder with a simple construction.

Besides, as another embodiment of the present invention, the biasing means may be preferably implemented by elastic modules.

Furthermore, as another embodiment of the present invention, it is preferable that a bracket may be set on the buccal side of each tooth of the lateral teeth, and that the wire may be attached to each bracket. In this case, it can be prevented that a load due to the biasing is applied to only one tooth of the lateral teeth.

BRIEF DESCRIPTION OF THE DRAWINGS

FIG. 4 is a perspective view of essential part of FIG. 3;

FIGS. 5A, 5B and 5C are explanatory views of operation of the orthodontic appliance shown in FIG. 1;

FIG. 7 is a schematic view of the inside of the oral cavity fitted with a prior-art orthodontic appliance, showing a case in which the wire and the brackets are set on the lingual side of individual teeth; and FIG. 8 is a schematic view showing the inside of the oral cavity fitted with a prior-art orthodontic appliance, showing a biasing state by elastic modules.

BEST MODE FOR CARRYING OUT THE INVENTION

Figure 1:
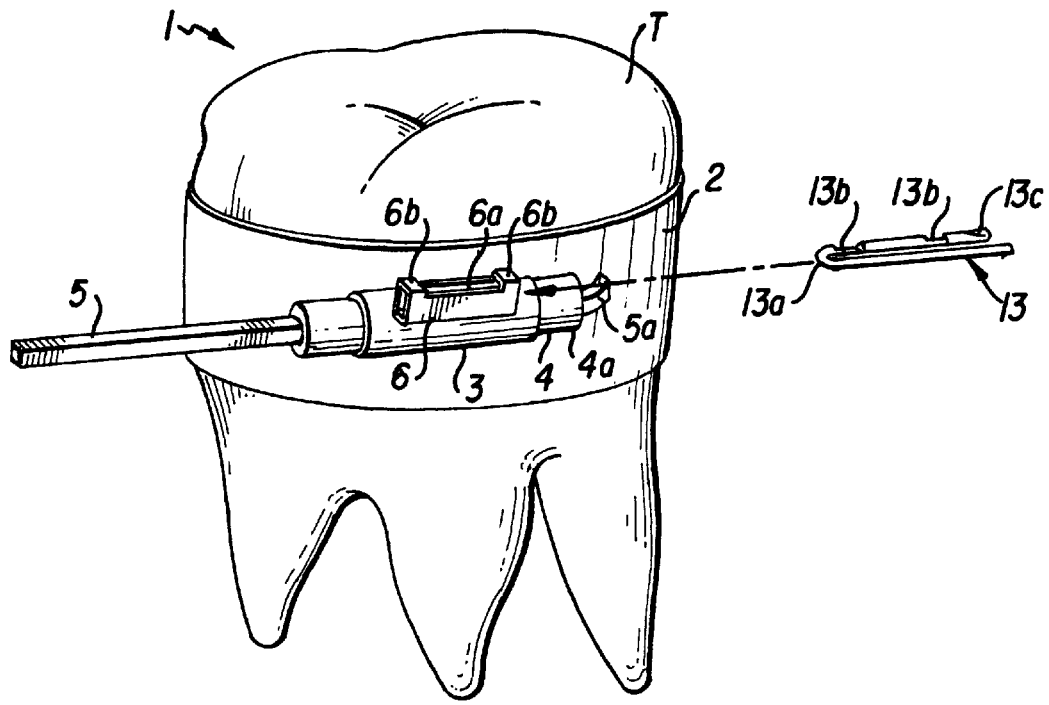
FIG. 1 is a perspective view showing an embodiment of the orthodontic appliance according to the present invention.
Figure 2:
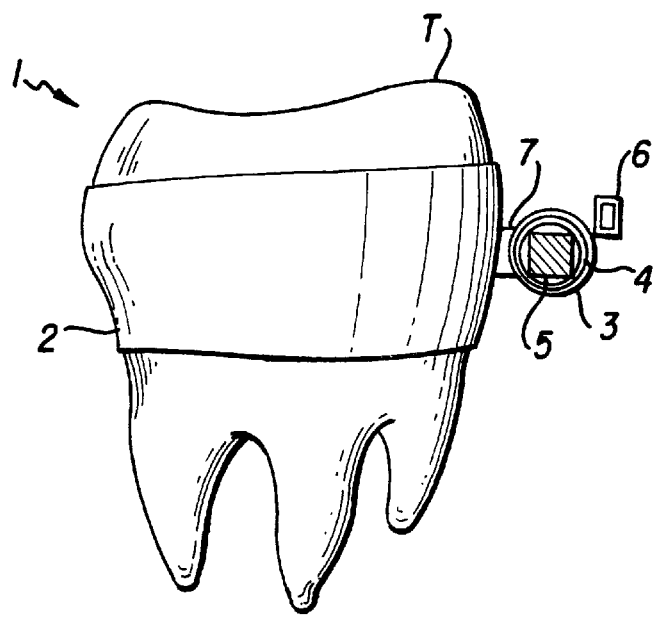
FIG. 2 is a view showing the orthodontic appliance of FIG. 1, as viewed in a direction in which a wire is inserted.
Figure 3:
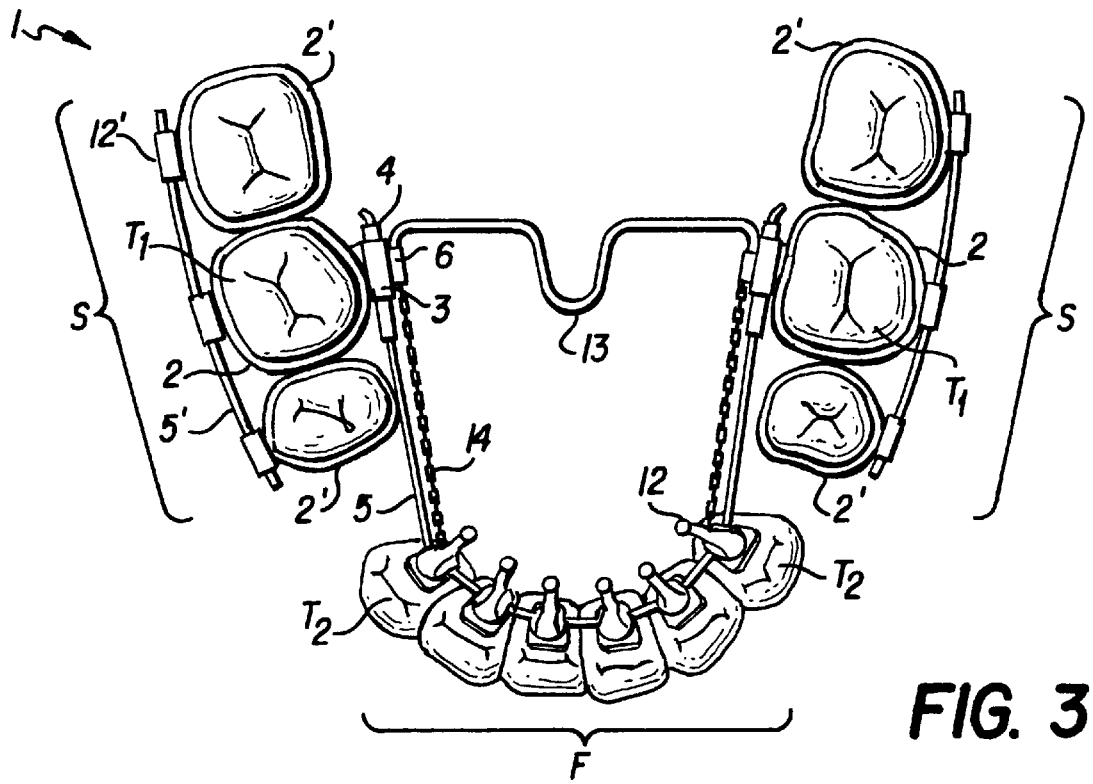
FIG. 3 is a plan view showing the inside of the oral cavity fitted with the orthodontic appliance according to the present invention.
Figure 6:
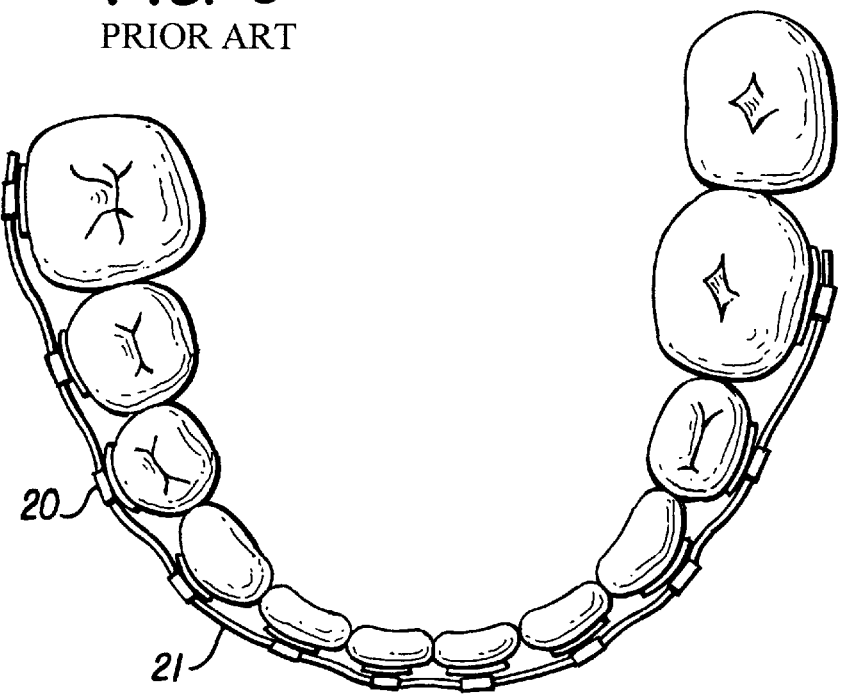
FIG. 6 is a schematic view showing the inside of the oral cavity fitted with a prior-art orthodontic appliance, showing a case in which the wire and the brackets are set on the buccal side of individual teeth.

FIGS. 1 and 2 show an embodiment of an orthodontic appliance 1 according to the present invention, and FIG. 3 shows the inside of the oral cavity fitted with the orthodontic appliance 1.

This embodiment is typified by, for example, a case in which after the first premolar tooth is extracted, anterior teeth F is retracted toward lateral teeth S as shown in FIG. 3 so as to close spaces resulting from the tooth extraction, by which the tooth alignment is accomplished.

A tooth T shown in FIG. 1 is one tooth belonging to the lateral teeth and, normally, the first molar tooth $T_1$ is selected therefor.

A metal band 2 is set around the tooth $T_1$. Further, a circular-cylindrical outer cylinder 3 is fixed on the lingual side of the band 2 via, for example, a torque-in base 7 as a coupling portion. The outer cylinder 3 has a length of 2 to 10 mm, preferably 4 to 7 mm, and an inside diameter of 0.8 to 2.0 mm, preferably about 1.0 to 1.3 mm, as an example. To the outer cylinder 3, a slidable inner cylinder 4 is further fitted into the outer cylinder 3. The inner cylinder 4 is formed in a circular-cylindrical shape like the outer cylinder 3, and longer than the outer cylinder 3. As an example, the length of the inner cylinder 4 is set to a length selected, as required, from within a range of 5 to 30 mm, preferably 8 to 20 mm, more preferably 10 to 15 mm, and its inside diameter is set so as to allow the insertion of a later-described wire 5, for example, to 0.7 mm. In this embodiment, the outer cylinder 3 and the inner cylinder 4 are provided on the lingual side of teeth for fear that the appearance of the teeth might be spoiled. However, the outer and inner cylinders may be provided on the buccal side of the teeth. In addition, the outer cylinder 3 and the inner cylinder 4 may be formed into various cylindrical shapes such as elliptical or polygonal cylindrical shapes, without being limited to circular cylindrical, whereas the outer cylinder 3 and the inner cylinder 4 are preferably of the same type of shape. Further, the outer cylinder 3 and the inner cylinder 4 may be changed also in dimensions as required.

A wire 5 is inserted through the inner cylinder 4. The wire 5 is made of metal, preferably stainless steel, and has a rectangular cross section as shown in FIG. 2. As shown in FIG. 3, the wire 5 is fixed to each tooth of the anterior teeth F via a bracket 12, and extended toward right and left lateral teeth S. The wire 5, after being inserted through the inner cylinder 4 as described above, has its fore end bent at an open end portion 4a of the inner cylinder 4, forming a bent portion 5a, by which the wire 5 is fixed to the open end portion 4a of the inner cylinder 4. Otherwise, the wire 5 may be fixed to the inner cylinder 4 by crimping the fore end of the wire 5 so that a flat crushed portion is formed. Further, by inserting a curved wire 5 into the inner cylinder 4, the wire 5 can be frictionally fitted and thereby fixed to the inner cylinder 4.

A circular-cylindrical or quadrilateral-cylindrical lingual sheath 6 is fixed to the outer cylinder 3. In the right and left lingual sheaths 6, an engaging hole 6a for inserting and fixing a trans-palatal bar 13 is formed in upper part.

The trans-palatal bar 13 is provided for aligning teeth correctly by rotating the first molar tooth $T_1$, i.e., tooth aligning around an axis line vertical to the occlusal surface of each irregular teeth, for correcting the distance between the right and left first molar teeth $T_1$, and for holding the first molar teeth $T_1$ themselves in position. The trans-palatal bar 13 is bent at a proximity to an end portion of linear extension, thus forming a spring hook portion 13a for fixing the trans-palatal bar 13 into the lingual sheath 6. On top of the spring hook portion 13a, are formed shallow cutouts 13b with which engaging surface portions 6b, 6b on both sides of the engaging hole 6a of the lingual sheath 6 are to be fitted. Also, an end portion of the spring hook portion 13a is crimped to form a flat crushed portion 13c. It is noted that the lingual sheath 6 and the trans-palatal bar 13 may also be fixed to each other by means of welding or brazing.

The outer cylinder 3 and the bracket 12 are coupled to each other via an elastic chain 14 as a biasing means implemented by a continuous, generally annular rubber. As shown in FIG. 4, the bracket 12 comprises a base plate portion 15 for fixing to a tooth and a fitting portion 16 for fitting the wire 5 and the elastic chain 14. The fitting portion 16 has a cutout portion 16a for inserting and holding the wire 5 in lower part of the base plate portion 15. Also, a hook portion 16b is formed so as to protrude downward from an outer portion of the fitting portion 16.

Next, a method of setting the orthodontic appliance 1 according to the present invention to teeth is described below.

As shown in FIG. 1, the metal band 2 is first attached to one tooth among the right or left lateral teeth (the first molar tooth $T_1$ in this embodiment), and the metal band 2' is set to each of the other teeth. The outer cylinder 3 is then attached to the metal band 2 by welding or brazing or the like. Otherwise, the metal band 2 with the outer cylinder 3 fitted thereto in advance may be attached to the tooth T. To the individual teeth of the lateral teeth S, brackets 12 are set on the buccal side of the metal bands 2, 2', and a wire 5' is also attached to these brackets 12'.

Next, as in the conventional method, the base plate part 15 of the bracket 12 is bonded and thereby fixed on the lingual side of each tooth of the anterior teeth F. Besides, the wire 5 is fitted to the cutout portion 16a of the fitting portion 16 of each of these brackets 12, and both ends of the wire 5 are extended toward the lingual side of the lateral teeth S. Then, the wire 5 is inserted into the inner cylinder 4, and after that, the inner cylinder 4 is inserted into the outer cylinder 3. The fore end 5a of the wire 5 is protruding at the open end of the inner cylinder 4. Therefore, this fore end 5a is bent and hooked to the open end portion 4a, by which the inner cylinder 4 is fixed to the wire 5 and the wire 5 is prevented from pulling off.

The lingual sheath 6 is fitted to the outer cylinder 3 in advance by welding or brazing in a specified setting. The trans-palatal bar 13 is attached so as to stretch over the right and left lingual sheaths 6 by being inserted and fitted thereto from backward. Further, one end of the elastic chain 14 is fixed by being hooked to the outer cylinder 3 side, for example, to one end portion of the spring hook portion 13a protruding from the lingual sheath 6, as shown in FIG. 4. The other end of the elastic chain 14 is fixed by being hooked to the hook portion 16b of the bracket 12 fixed to one tooth (a canine tooth $T_2$ in this embodiment) among the anterior teeth F, and then the anterior teeth F is biased toward the lateral teeth S. Thus, the setting of the orthodontic appliance 1 to teeth is completed.

In the orthodontic appliance 1 set by the above procedure, the inner cylinder 4 is at first protruding toward the anterior teeth F relative to the outer cylinder 3, as shown in FIG. 5A. As time elapses, however, the inner cylinder 4 gradually moves backward as shown in FIGS. 5B, 5C. Because this movement allows the inner cylinder 4 to slide within the outer cylinder 3 along with the wire 5, these serve as an absorbing means, eliminating the need of adjusting the length of the wire 5 during the tooth alignment. In addition, if the backward movement of the wire 5 causes the end portion of the wire 5 to protrude beyond the outer cylinder 3 so as to come into contact with the gums, it is preferable to cut the end portion of the wire 5 shorter. Also, early in the stage where the orthodontic appliance 1 is set, the wire 5 can be supported by the inner cylinder 4 extending toward the anterior teeth F, so that the anterior teeth and the lateral teeth can be firmly connected to each other while preventing any deflection of the wire 5.

I claim:

1. An orthodontic appliance comprising:

a band to be set around one tooth of lateral teeth;

an outer cylinder fixed to the band;

an inner cylinder formed longer than the outer cylinder and supported slidably within the outer cylinder;

a wire fixed to each tooth of anterior teeth via a bracket and extended toward the lateral teeth, and inserted through the inner cylinder; and biasing means attached between the outer cylinder and the bracket and serving for biasing the anterior teeth toward the lateral teeth, wherein the inner cylinder is fixed at an open end portion thereof to the wire.

2. The orthodontic appliance according to claim 1, wherein the outer cylinder and the inner cylinder are located on a lingual side of the lateral teeth.

3. The orthodontic appliance according to claim 1, wherein a lingual sheath is fixed to the outer cylinder.

4. The orthodontic appliance according to claim 3, wherein a trans-palatal bar is attached to the lingual sheath.

5. The orthodontic appliance according to claim 1, wherein the inner cylinder is fixed to the wire by bending the wire protruding from the open end of the inner cylinder.

6. The orthodontic appliance according to claim 1, wherein the biasing means is implemented by an elastic.

7. The orthodontic appliance according to claim 1, wherein a bracket is set on the buccal side of each tooth of the lateral teeth, and the wire is attached to each bracket.

* * * * *